United States Patent [19]

Nassar et al.

[11] Patent Number: 5,389,107
[45] Date of Patent: Feb. 14, 1995

[54] SHOCK ABSORBENT PROSTHETIC HIP JOINT

[75] Inventors: Antoine A. Nassar, 4631 Landings Dr., Fort Meyers, Fla. 33919; Eugene C. Eckstein, Miami, Fla.

[73] Assignee: Antoine A. Nassar, Fort Myers, Fla.

[21] Appl. No.: 54,463

[22] Filed: Apr. 28, 1993

Related U.S. Application Data

[63] Continuation of Ser. No. 881,259, May 11, 1992, abandoned.

[51] Int. Cl.[6] .............................. A61F 2/36; A61F 2/32; A61F 2/30
[52] U.S. Cl. .................................. 623/23; 623/22; 623/18
[58] Field of Search .................. 623/16, 18, 22, 23

[56] References Cited

U.S. PATENT DOCUMENTS

| 2,682,265 | 6/1954 | Collison | 623/23 |
| 3,648,294 | 3/1972 | Shahrestani | 623/22 |
| 3,658,056 | 4/1972 | Huggler et al. | 623/22 |
| 3,874,003 | 4/1975 | Moser et al. | 623/23 |
| 4,032,994 | 7/1977 | Frey | 623/22 |
| 4,065,817 | 1/1978 | Branemark | 623/22 |
| 4,129,903 | 12/1978 | Huggler | 623/23 |
| 4,662,891 | 5/1987 | Noiles | 623/22 |
| 5,007,935 | 4/1991 | Vincent et al. | 623/22 |
| 5,071,435 | 12/1991 | Fuchs et al. | 623/22 |

FOREIGN PATENT DOCUMENTS

| 0170982 | 2/1986 | European Pat. Off. | 623/22 |
| 0346294 | 12/1989 | European Pat. Off. | 623/22 |
| 2304399 | 8/1974 | Germany | 623/22 |
| 3033227 | 4/1982 | Germany | 623/22 |

Primary Examiner—Randall L. Green
Assistant Examiner—Dinh X. Nguyen
Attorney, Agent, or Firm—William E. Noonan

[57] ABSTRACT

A shock absorbent prosthetic hip joint is provided, including a socket section that is attachable to the pelvic bone and a ball section that is pivotably engaged with the socket section. There is a first shock absorber section attached to the ball section and a second shock absorber section attached to an upper part of the femur bone. The second shock absorber section slidably engages the first shock absorber section. A spring is disposed between the first and second shock absorber sections for cushioning a compressive force applied between the femur and pelvic bones.

11 Claims, 4 Drawing Sheets

SHOCK ABSORBENT PROSTHETIC HIP JOINT

This application is a continuation of application Ser. No. 07/881,259, filed May 11, 1992, now abandoned.

FIELD OF THE INVENTION

This invention relates to a shock absorbent prosthetic hip joint, which significantly dampens the force of impact caused by walking, running or similar activities.

BACKGROUND OF THE INVENTION

Surgically implanted replacement or prosthetic hips are presently in widespread use. Conventional hip prostheses typically include a socket that is attached to the pelvic bone and an insert that fits in and extends from an opening in the upper end of the femur. The outer end of the insert carries a ball that rotatably engages the socket to simulate the patient's natural hip joint.

During the course of strenuous activities such as running, jumping, playing tennis and even walking, repeated large compressive stresses are transmitted through the replacement hip and through the patient's knee. The jarring forces that cause the stresses can, over time, cause the hip apparatus to loosen. Eventually, corrective surgery may even be required. Moreover, the repeated force of impact on the prosthetic hip can cause fractures and be very painful to the patient.

Various known replacement hips have attempted to address the above problems by employing cushioning or dampening substances between the ball and socket of the artificial joint. However, such devices do not significantly lessen the detrimental effects of repeated compressive stress applied along the replacement hip. Debris generated by the impact force exerted on the joint also contributes to loosening of the prosthetic stem. In particular, such debris causes the bone cells to produce a lytic hormone to attack and dissolve the debris. Unfortunately, this hormone also attacks and dissolves the bone, thereby loosening the stem.

SUMMARY OF THE INVENTION

It is therefore an object of the present invention to provide an improved shock absorbent prosthetic hip joint.

It is a further object of this invention to provide a prosthetic hip joint that significantly dampens the jarring force and impact load exerted on the joint as a result of walking, running and similar activities.

It is a further object of this invention to provide a prosthetic hip joint that exhibits a relatively long life, resists loosening and reduces the need for corrective surgery.

It is a further object of this invention to provide a prosthetic hip that significantly reduces the pain which a hip replacement patient experiences when walking, running and engaging in similar strenuous activities involving the legs.

It is a further object of this invention to provide a prosthetic hip that reduces the transmitted impact on the knee joint.

It is a further object of this invention to provide a prosthetic hip joint with a femoral component that resists rotation relative to the femur.

It is a further object of this invention to provide a prosthetic hip joint that confines the collection of debris and allows the removal of such debris.

This invention results from a realization that an improved shock absorbent replacement hip joint may be achieved by employing a spring action between the shaft or stem that extends from the artificial ball of the hip and the insert or other piece that is attached to the femur.

This invention features a shock absorbent prosthetic hip joint that includes a socket section, which is attachable to the pelvic bone. A ball section is pivotably engaged with the socket section. A first shock absorber section is attached to the ball section and a second shock absorber section is attached to an upper part of the femur bone. The second shock absorber section has means for slidably engaging complementary means in the first shock absorber section. There are spring means disposed between the first and second shock absorber sections for cushioning a compressive force applied between the pelvic and femur bones. Such a force may comprise the impact force generated by walking or running. However, even when the patient is at rest, some compressive force or load may be exerted because of muscular loads that always act across the joint. The spring means of this invention serves to cushion all such compressive forces.

In a preferred embodiment the first shock absorber section includes an elongate element that extends coaxially from the ball section. The second shock absorber section may include an elongate insert received by an opening in the femur bone and having an axial chamber formed therein for receiving the elongate element. The spring means may be disposed within the chamber and extend between an inside end of the chamber and a distal end of the elongate element.

The means for slidably engaging may include an elongate chamber and the complementary means may include a piston mounted for reciprocating slidable motion in the chamber. The means for slidably engaging may include a slide pin extending through the chamber and the piston may have a generally axial groove for slidably receiving the slide pin. The spring means may include a helical compression spring disposed about the slide pin and extending between the distal end of the piston and an inside end of the chamber. The spring means may further include a helical compression spring disposed in the groove and extending between an inside end of the groove and a distal end of the slide pin. In certain embodiments the slide pin may extend through and from the femur bone. A mounting plate may be attached to the slide pin for engaging the outside surface of the femur bone and means may be provided for securing the mounting plate to the femur bone.

The spring means may alternatively include a volumetric spring, such as a non-crosslinked paste-like material. The chamber may include a chamfered upper end. A wear resistant, low friction bushing or a surface treatment may be disposed about the chamber. A lubricant may be disposed between the piston and the wall of the chamber.

DETAILED DESCRIPTION OF PREFERRED EMBODIMENTS

Other objects, features and advantages will occur from the following description of a preferred embodiment and the accompanying drawings in which.

Figure 1:
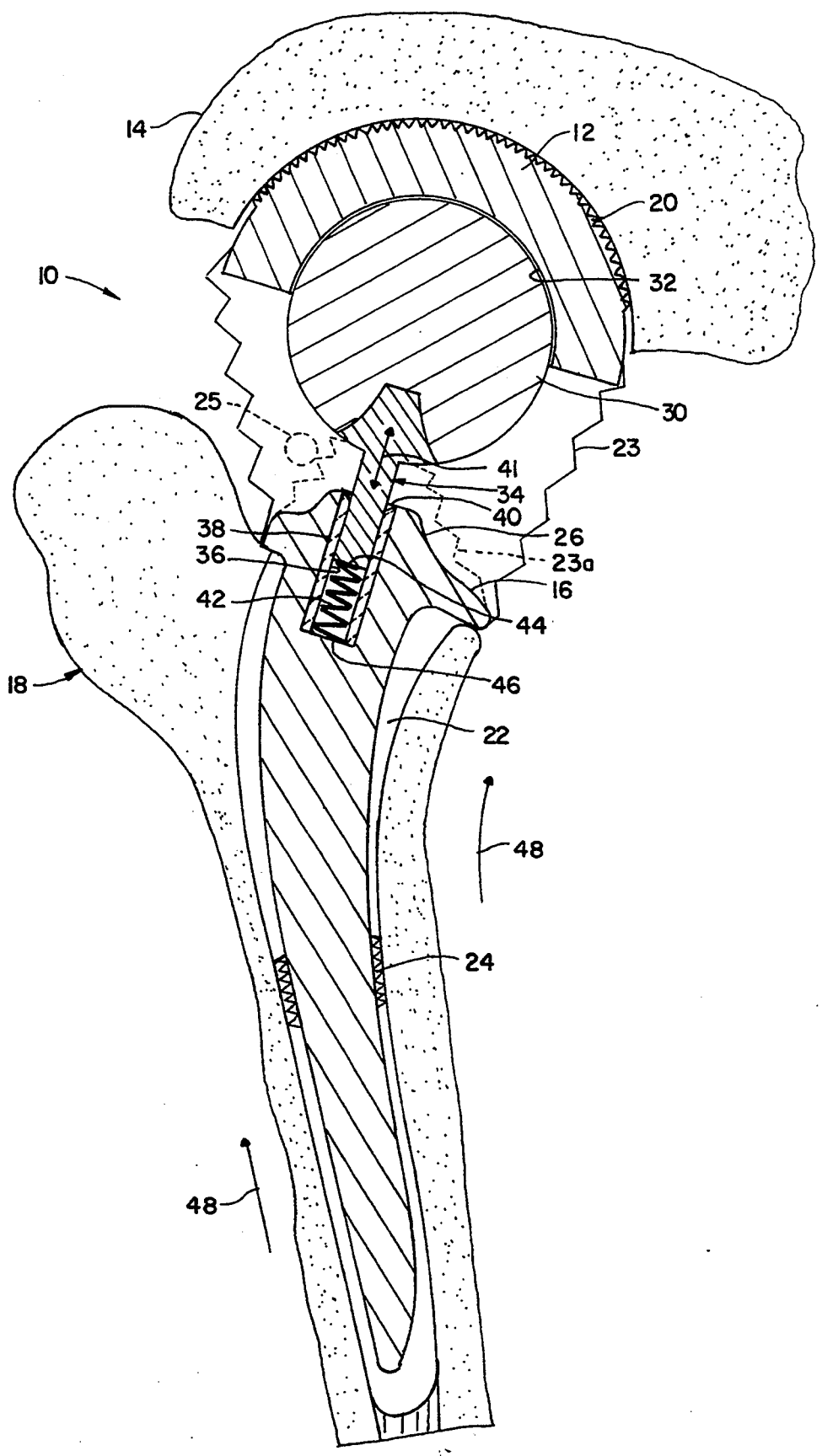
FIG. 1 is an elevational, cross sectional view of a shock absorbent prosthetic hip joint apparatus according to this invention.

There is shown in FIG. 1 a prosthetic hip joint apparatus 10 including a socket portion 12 that is secured to pelvic bone 14. More particularly, socket portion 12 is a conventional element that is commonly used in replacement hips. That element is fixed to pelvic bone 14 in a known manner and is provided with a knurled or rough outer cap 20 that resists slipping. Alternatively, the socket may comprise the natural socket that is formed in the pelvic bone. A ball portion 30 composed of titanium alloy, stainless steel or other durable materials known in the art is operably engaged with the spherical socket surface 32 of socket portion 12. A first shock absorber section comprising an elongate piston element 34 composed of a similar durable material is fixedly connected to and extends from ball portion 30. A second shock absorber section comprising an insert 16 is secured to the upper end of femur 18. Insert 16 includes an elongate shape and is tapered at its lower end such that it fits snugly within a cavity 22 of femur 18. A region 24 of the outside surface of insert 16 is knurled, stippled or otherwise rough so that it frictionally engages the walls of femur cavity 22. Cement may be added between the insert and the wall of the cavity. Alternatively, according to present technology, a secure cementless fit may be provided between insert 16 and femur 18. As a result, the insert is held securely in place within the femur bone. The upper end 26 of insert 16 protrudes slightly above the entrance of cavity 22. Both socket portion 12 and insert 16 are composed of a suitable material, such as titanium alloy or polished stainless steel, known to those skilled in the art of prosthetic hip devices.

A generally cylindrical bellows 23 is interconnected between socket portion 12 and upper end 26 of insert 16. The bellows is attached to the cap 20 and insert 16 by a suitable adhesive or other means of attachment. As a result, the shock absorbing apparatus of this invention is enclosed and protected from bodily fluids during use in the manner described more fully below. In alternative embodiments the bellows may be omitted.

Piston 34 is slidably received by an axial chamber 36 formed in the upper end of insert 16. More particularly, a bushing or sleeve 38 composed of a highly polished, low friction, wear resistant material, such as alumina or another ceramic, is mounted within chamber 36 proximate the entrance 40 of the chamber. Piston 34 extends into and is slidably engaged in close tolerance with the inside wall of bushing 38. As a result, piston 34 and attached ball 30 are slidable as directed by chamber 36, and as indicated by double-headed arrow 41.

A helical compression spring 42 is disposed within chamber 36 and extends between the distal end 44 of piston member 34 and the lower end 46 of chamber 36. A lubricant may be used within the chamber surrounding spring 42. From its normal unstressed condition, spring 42 is biased to urge piston 34 and ball 30 outwardly from chamber 36 in the direction of arrow 47 into an expanded condition. In response to a load or impact force exceeding a compressive threshold, indicated by arrows 48, being applied to femur 18, the inertia of the patient's pelvis and upper body resist the advance of insert 16 and the femur 18, thereby causing piston 34 to advance in chamber 36 and compress spring 42. The impulsive loading is cushioned due to the compression of spring 42. Preferably, in response to the impact, piston 34 travels a relatively large distance. When the force dissipates, spring 42 urges the ball and piston outwardly from chamber 36 such that piston 34 and ball 30 are returned to their normal position with ball 30 spaced apart from femur 18. As a result of the above actions, the force of impact exerted between the parts of joint 10 is attenuated significantly. Disruption and loosening of the hip prosthesis are minimized and pain is reduced.

The threshold force required to compress spring 42 is not a limitation of this invention and may be selected before the hip is implanted by selecting the length and tension of the spring.

Bellows 23 is attached to the acetabulum socket 12, permits normal joint motion, and expands and contracts with spring 42 to seal the device against bodily fluids and contained debris generated by frictional engagement of the parts. As a result, this prevents the formation of lytic hormones, which would tend to loosen the insert. The bellows may be constructed of a suitable compatible material and include an elastomeric, relatively dense plug 25 that permits, under fluoroscopy, the insertion of a needle to irrigate and remove debris. It also permits replacement of lubricant for the spring. In alternative embodiments, which lack a acetabular component (including socket 12 and cap 20) the bellows 23a may be attached to the base of ball 30 and the insert 16, as illustrated in phantom. This similarly encloses the piston, chamber and spring and protects these components against the collection of debris.

Figure 2A:
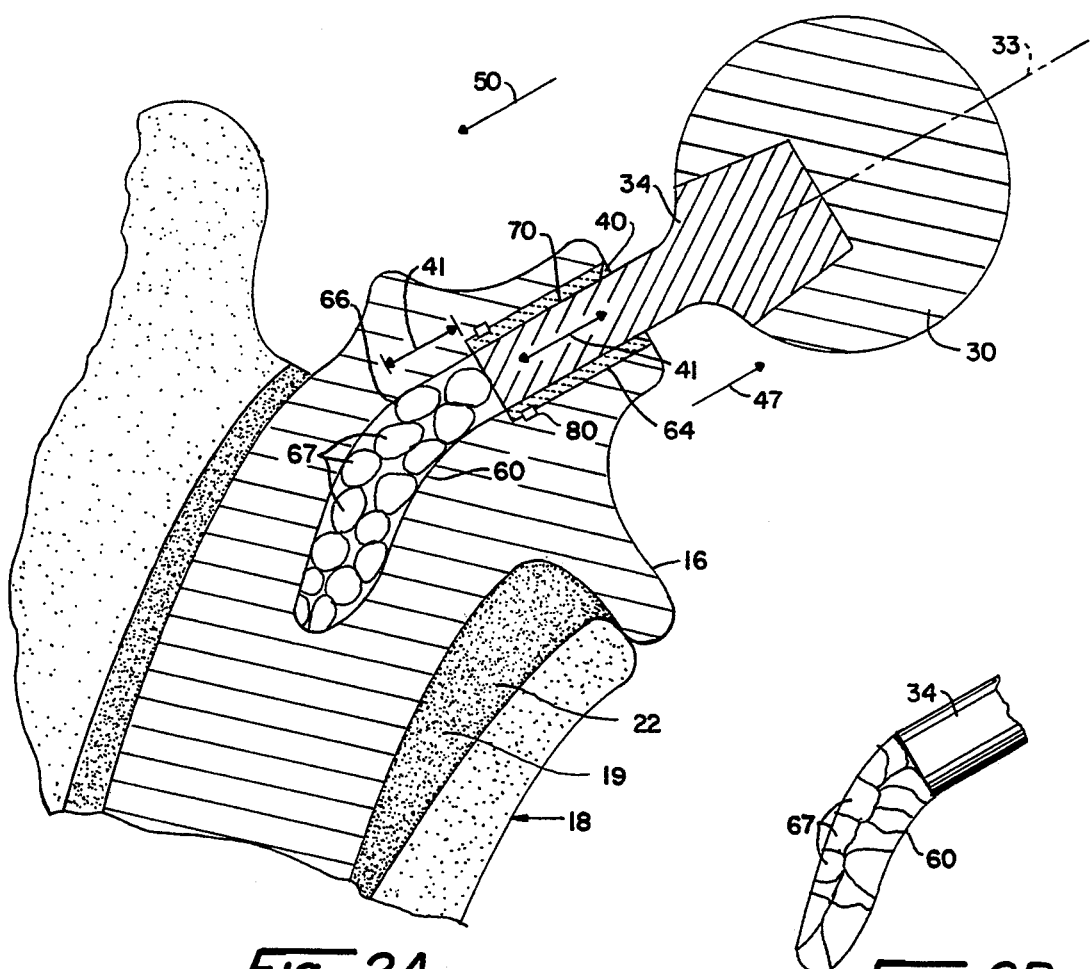
FIG. 2A is a cross sectional view of the upper end of an alternative preferred prosthetic hip joint apparatus according to this invention.
Figure 2B:
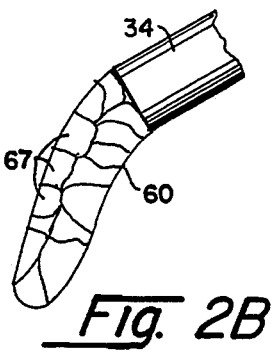
FIG. 2B is an elevational, cross sectional view of the apparatus of FIG. 2A in a compressed condition.

An alternative shock absorbent hip joint is shown in FIGS. 2A and 2B. In this embodiment, elements that are identical to those described in connection with FIG. 1 are again provided with like reference numbers. Insert 16 is again received within an opening 22 that is formed in the upper end of a femur bone 18. Cement or grout 19 may be employed to hold insert 16 securely in place. A generally axial chamber 60 is formed in the upper end of insert 16. A wear resistant alumina bushing or sleeve 64 is mounted within chamber 60 proximate the chamfered entrance 40 of the opening. A volumetric spring 66 is disposed within chamber 60 below bushing 64. Spring 66 comprises a plurality of resilient spherical elements 67 composed of a suitable elastomer such as silicone rubber or microcellular urethane. Silicone rubber is well suited for this operation. Such material includes a relatively low bulk modulus that permits a significant motion of the piston in response to an applied load.

Ball element 30, as previously described, includes a stem-like piston 34 that is attached to and extends generally axially therefrom. Piston 34 is received by bushing 64 and is slidable therein, along an axis 33, as indicated by double-headed arrow 41. To assist such sliding motion, a lubricant 70 may be provided within chamber 60 and between the inner surface of bushing 64 and the outer surface of piston 34. As piston 34 advances in chamber 60, in the direction of arrow 50, spheres 67 of spring 66 are compressed and, as the piston retracts in the direction of arrow 47, spheres 67 expand. An O-ring or other seal 80 is disposed about the lower end of bushing 64 to prevent lubricant 70 from passing along the outside surface of the bushing.

In operation, as compressive stress or force is applied to the prosthesis, piston 34 is advanced in the direction of arrow 50. As shown in FIG. 2B, volumetric spring 66 is compressed within chamber 60 by this advance of the piston such that the impact force exerted along the prosthesis is lessened or dampened due to motion of the spring. Because chamber 60 is bent to generally conform to the axis of insert 16, the strength and integrity of the insert are improved. If a generally straight chamber is used, as in the embodiment of FIG. 1, satisfactory results are achieved; however, because the chamber diverts from the axis of the insert, the insert may be weakened somewhat. After the impact force dissipates and advance of piston ceases, the resilience of spring 66 causes the piston 34 and attached ball 30 to retract outwardly from chamber 60 in the direction of arrow 47 until they return to the position shown in FIG. 2B. As a result, a cushioning or buffering effect is provided to the prosthetic device.

In alternative embodiments, spring 60 may comprise a solid piece of silicone, or a closed cell foam. However, spheres 67 are preferred because the gaps among them can be reduced in size or even closed due to the lateral expansion of the compressed spheres, as shown in FIG. 2B. A solid spring has no room for expansion. As a result, added friction may be exhibited between the spring and the chamber. Such friction can create debris, which can cause premature deterioration of the replacement hip.

Figure 3A:
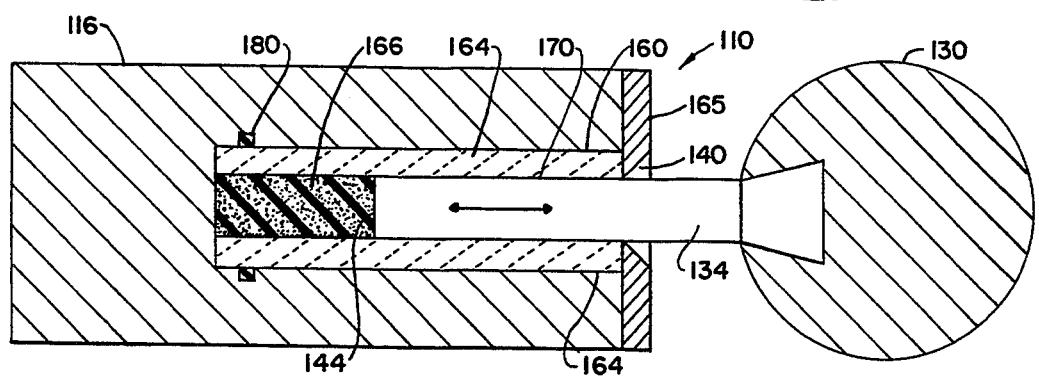
FIG. 3A is an elevational diagrammatic view of a further preferred shock absorbent hip joint.
Figure 3B:
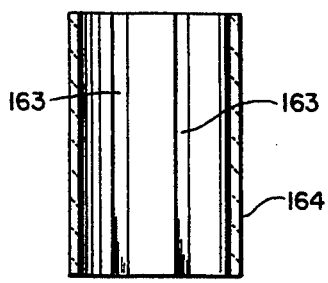
FIG. 3B is a cross sectional view of a preferred sleeve.

In FIG. 3A an alternative schematic arrangement is depicted wherein the opening in the femoral insert 116 is straight and a bushing 164 extends for the entire length of the chamber 160. In particular, the shock absorber 110 includes an insert 116 that is depicted schematically but is generally analogous to the insert previously described. Elongate axial chamber 160 is formed in the upper end of insert 116 and sleeve or bushing 164, as previously described, extends for the entire length of chamber 160. A retaining cap 165 is secured to the upper end of the insert by appropriate adhesive means. Cap 165 extends over bushing 164 such that the bushing is held in place within opening 160. A chamfered entrance 140 is formed through retaining cap 165 and is in communication with the central channel formed through bushing 164. A volumetric spring 166 composed of a non-crosslinked paste-like material, such as silicone gum or a similar material, is disposed within the central channel of bushing 164. This material also resists impact and friction with the bushing. A piston 134, which is secured to a rotatable ball joint 130, extends through bushing 164 and is slidable therein against spring 166. A lubricant 170, which is immiscible with spring 166, is disposed between piston 134 and the inner wall of bushing 164. This lubricant, which may comprise a perfluorochemical oil, helps the piston to advance and retract within the bushing. It also blocks debris from penetrating the apparatus. During advancement, the lower end 144 of the piston bears against and compresses spring 166 to cushion the force on the prosthetic device. A seal 180 is disposed about the outside surface of bushing 164 proximate the lower end of the bushing. This seal prevents lubricant material from seeping around the outside surface of the bushing. Chamfered entrance 140 serves as a reservoir for collecting lubricant 170 that is forced out of bushing 164 during advancement of piston 134. As shown in FIG. 3B, bushing 164 may include longitudinal channels 163, which accommodate and permit freer flow of lubricant 170 during operation of the piston 134.

Figure 4:
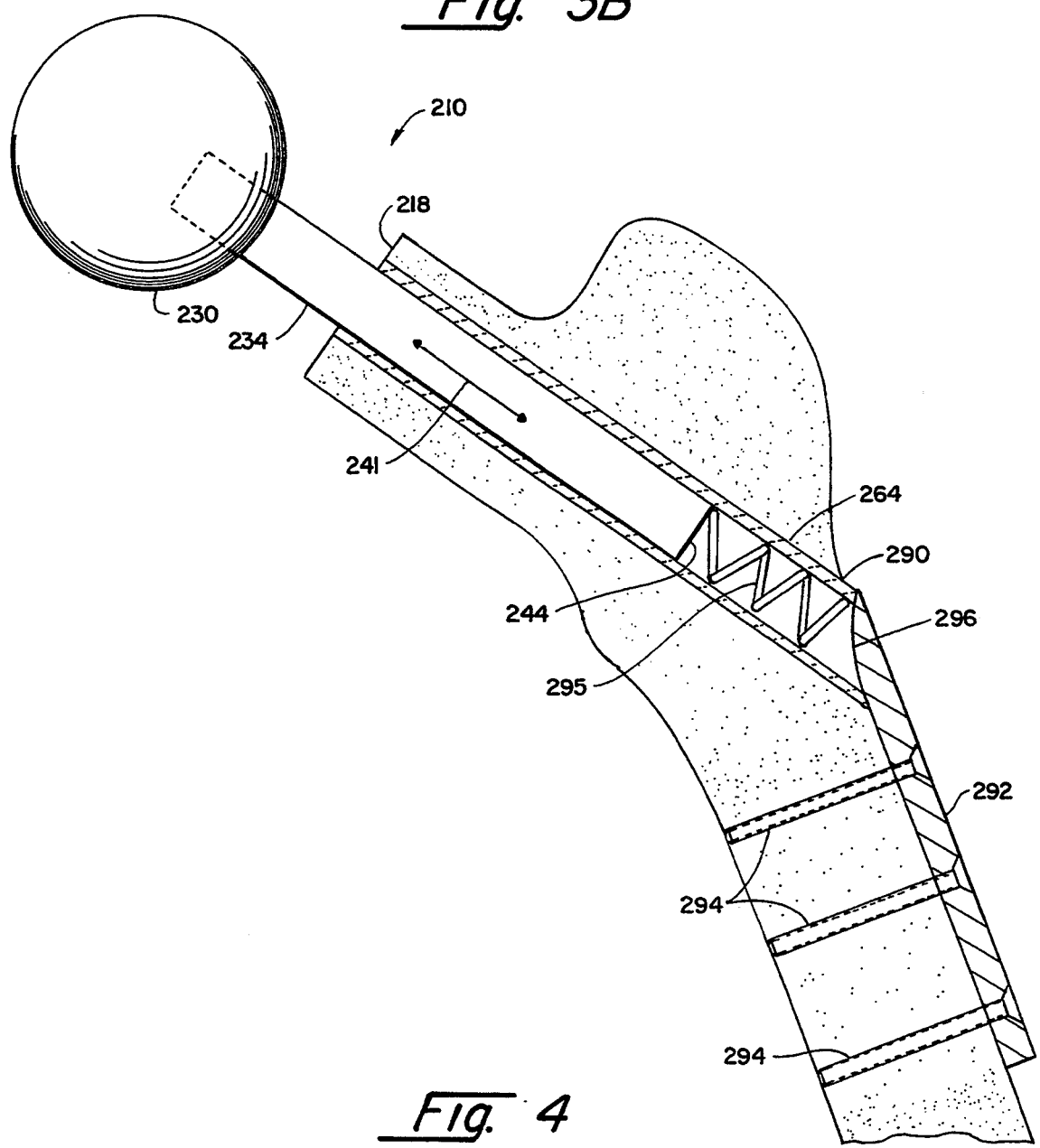
FIG. 4 is an elevational, cross sectional view of an alternative shock absorbent prosthetic hip, featuring a cortical plate.

In the alternative embodiment shown in FIG. 4, shock absorbent hip joint 210 again includes a ball portion 230 and an attached piston 234. However, in this embodiment, no insert is provided in the upper end of the femur. Instead, an elongate bushing or sleeve 264 extends from the upper end of femur 218 through the bone to a lower point 290 in the femur. Piston 234 is slidably received within bushing 264, as indicated by double-headed arrow 241.

A cortical plate 292 is secured to a lower portion of femur 218 by appropriate screws 294. Plate 292 is also attached to the lower end of bushing 264. A helical spring 295 is disposed between the lower end 244 of piston 234 and the upper end 296 of cortical plate 292. As a result, when compressive, impacting force is applied to the femur, the piston 234 advances within bushing 264 and spring 295 is compressed. As the force subsides, the bias of the spring eventually causes the compressed spring to expand so that the piston 234 and attached ball 230 are retracted within the bushing 264. As a result, the impact is cushioned.

Figure 5:
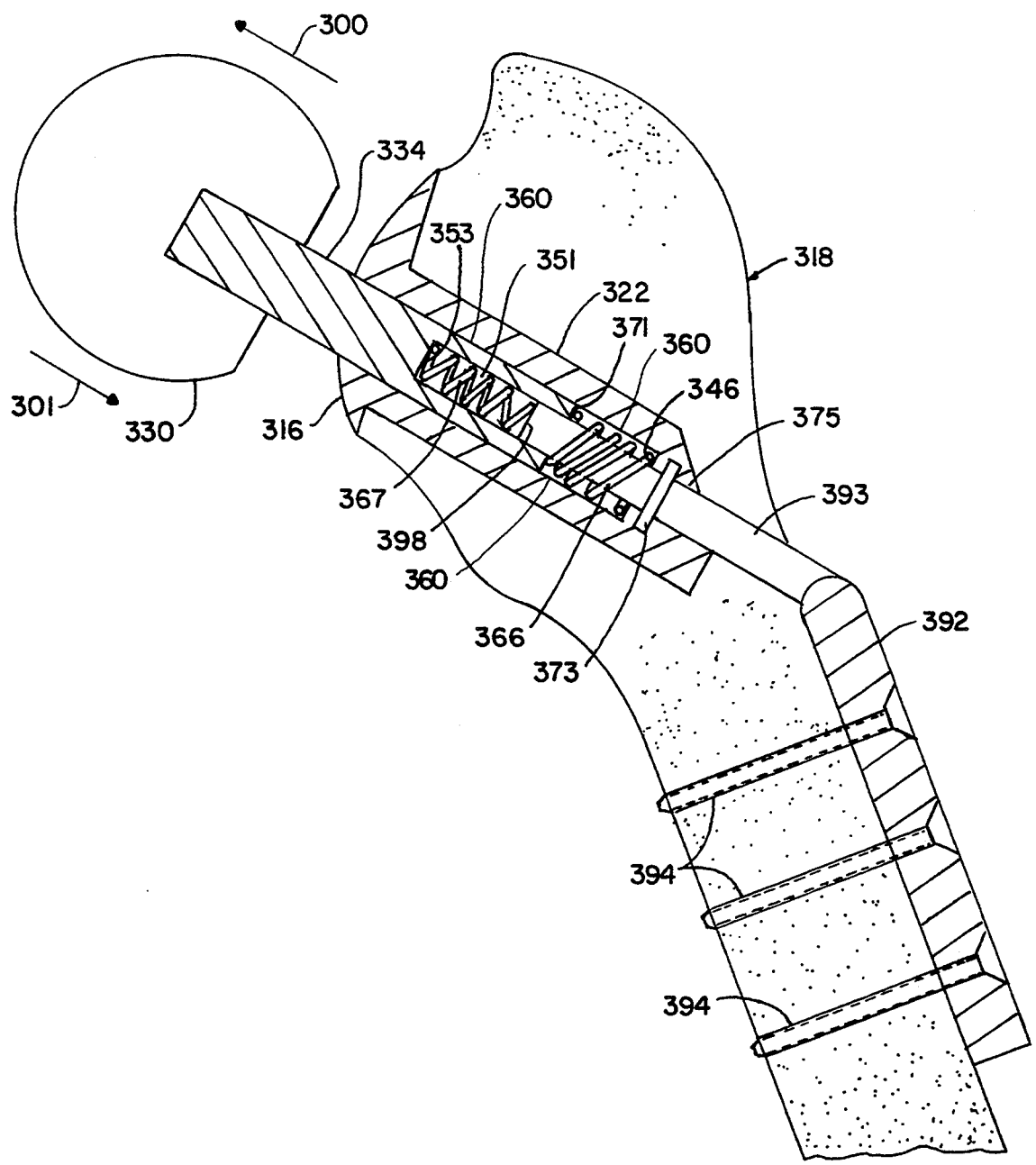
FIG. 5 is an elevational, cross sectional view of still another shock absorbent prosthesis according to this invention featuring an elongate pin attached to the cortical plate and a pair of helical springs for providing shock absorption.

An alternative embodiment that employs a cortical plate is illustrated in FIG. 5. Therein, an insert 316 is secured within an opening 322 in the upper end of femur 318. Insert 316 includes a generally axial chamber 360. A cortical plate 392 is secured to femur 318 by screws 394. A pin 393 is secured to the upper end of cortical plate 392 and extends into and through the femur 318 and through an opening 375 into chamber 360 of insert 316.

Ball element 330 has attached thereto an elongate piston 334 that extends into and is longitudinally slidable within axial chamber 360 of insert 316. Piston 334 includes a generally axial groove 351 that slidably receives pin 393. A first helical compression spring 366 is disposed about pin 393 and extends between the distal end 371 of piston 334 and the inner end 346 of axial chamber 360. A second helical spring 367 is disposed within groove 351 of piston 334 and extends from the inner end 353 of groove 351 to the end 398 of pin 393. Springs 366 and 367 are biased such that piston 334 is urged in the direction of arrow 300 into an retracted condition relative to insert 316. The piston remains slidably engaged with pin 393. A suitable lubricant is added to chamber 360 and groove 351 to reduce friction caused by the helical compression springs. A reciprocating seal 373 is formed about pin 393. Another reciprocating seal could be used between piston 334 and insert 316.

In operation, as the patient walks or runs, the impact force causes ball 330 (and the socket and bones that it supports) to be driven in the direction of arrow 301. Piston 334 advances to compress springs 366 and 367 and those springs act to absorb the shock impact force. As the force dissipates the springs resume their normal biased conditions to urge ball 330 in the reverse direction indicated by arrow 300.

The embodiments disclosed in FIGS. 4 and 5 provide several advantages over the embodiments which employ a femoral insert. In particular, the stem position of the prosthetic device can be rotated much less readily if a cortical plate is utilized. Plates 292 and 392 in FIGS. 4 and 5, respectively, restrain the rotation and avoid the problem of loosening of the insert, which can occur when conventional hip prosthesis are rotated. Moreover, in the two spring embodiment shown in FIG. 5 the springs 366 and 367 permit the load to be split between the upper portion of the femur 318 and the mounting plate 392. In particular, the slide fit of pin 393 into insert 316 permits controlled compressive loading of the upper portion of femur 318.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. A shock absorbent prosthetic hip joint comprising:
   a ball section that is pivotably engaged with a socket section connected to a pelvic bone;
   a first shock absorber section attached to and extending from said ball section and including a piston that has a substantially solid cross section;
   a second shock absorber section attached to an upper part of a femur bone and including an insert configured for insertion into the intramedullary cavity, said insert having an axial chamber formed therein for slidably receiving said piston and permitting said piston to reciprocate in said chamber; and
   spring means disposed in said chamber and interengaging a distal end surface of said piston and an inner end of said axial chamber, said distal end surface faces a direction generally opposite to said ball section; said spring means being configured for biasing said first and second shock absorber sections into an expanded condition wherein said ball section is spaced relatively apart from the femur bone
   and being responsive to application of a compressive load between the femur and pelvic bones for allowing said first and second shock absorber sections to slide into a compressed condition to cushion said compressive load.

2. The apparatus of claim 1 in which said spring means include a volumetric spring.

3. The apparatus of claim 2 in which said volumetric spring includes a non-crosslinked paste-like material.

4. The apparatus of claim 1 in which said spring means are disposed within said chamber and extend between an inside end of said chamber and a distal end of said elongate element.

5. The apparatus of claim 1 in which said chamber includes a chamfered upper end.

6. The apparatus of claim 1 further including a friction resistant bushing disposed about said chamber.

7. The apparatus of claim 1 in which a lubricant is disposed between said piston and the wall of said chamber.

8. The apparatus of claim 1 in which said spring means include a plurality of resilient spherical elements disposed in said chamber.

9. The apparatus of claim 1 further including means interconnected between said socket section and said second shock absorber section for enclosing said spring means.

10. The apparatus of claim 9 in which said means for enclosing include a bellows element.

11. A shock absorbent prosthetic hip joint comprising:
    a socket section that is attachable to a pelvic bone;
    a ball section pivotably engaged with said socket section;
    a first shock absorber section attached to said ball section;
    a second shock absorber section attached to an upper part of a femur bone and having means for slidably engaging complementary means in said first shock absorber section, said means for slidably engaging including an elongate chamber and said complementary means including a piston mounted for reciprocating slidable motion in said chamber and further including a slide pin extending through said chamber, said piston having a generally axial groove for slidably receiving said slide pin; and
    spring means disposed between said first and second shock absorber sections for biasing said first and second shock absorber sections into an expanded condition wherein said ball section is spaced relatively apart from said femur bone; said spring means being responsive to application of a compressive load between the femur and pelvic bone for allowing said first and second shock absorber sections to slide into a compressed condition to cushion said compressive load;
    said spring means including a first helical compression spring disposed about said slide pin and extending between a distal end of said piston and an inside end of said chamber and a second helical compression spring disposed in said groove and extending between an inside end of said groove and a distal end of said slide pin; said slide pin extending through and from the femur bone and said second shock absorber section further including a mounting plate attached to said slide pin for engaging the outside surface of the femur bone and means for securing said mounting plate to the femur bone.

* * * * *